(12) United States Patent
Bhansali et al.

(10) Patent No.: US 10,517,533 B2
(45) Date of Patent: Dec. 31, 2019

(54) MATERIALS AND METHODS FOR DETECTING AND MONITORING EDEMA AND RELATED CONDITIONS

(71) Applicants: Shekhar Bhansali, Weston, FL (US); Karina Rincon, Doral, FL (US); Jessica Ramella-Roman, Miami Beach, FL (US); Sanjukta Bhanja, Tampa, FL (US)

(72) Inventors: Shekhar Bhansali, Weston, FL (US); Karina Rincon, Doral, FL (US); Jessica Ramella-Roman, Miami Beach, FL (US); Sanjukta Bhanja, Tampa, FL (US)

(73) Assignees: The Florida International University Board of Trustees, Miami, FL (US); University of South Florida, Tampa, FL (US)

(*) Notice: Subject to any disclaimer, the term of this patent is extended or adjusted under 35 U.S.C. 154(b) by 126 days.

(21) Appl. No.: 15/155,881

(22) Filed: May 16, 2016

(65) Prior Publication Data

US 2016/0331314 A1    Nov. 17, 2016

Related U.S. Application Data

(60) Provisional application No. 62/162,520, filed on May 15, 2015.

(51) Int. Cl.
*A61B 5/01* (2006.01)
*A61B 5/00* (2006.01)
(Continued)

(52) U.S. Cl.
CPC .......... *A61B 5/4878* (2013.01); *A61B 5/0205* (2013.01); *A61B 5/0261* (2013.01);
(Continued)

(58) Field of Classification Search
CPC ........... A61B 5/0075; A61B 5/01; A61B 5/04; A61N 1/08; A61N 1/36014; A61N 5/0616; A61N 1/36003; A61N 1/328
(Continued)

(56) References Cited

U.S. PATENT DOCUMENTS

| 8,731,657 B1* | 5/2014 | Shambayati ....... A61N 1/36014 128/908 |
| 2013/0041235 A1* | 2/2013 | Rogers ................. A61B 5/6867 600/306 |

(Continued)

OTHER PUBLICATIONS

Bellini, C. et al., "Lymphatic Dysplasias in Newborns and Children: The Role of Lymphoscintigraphy." *The Journal of Pediatrics*, Apr. 2008, 152:587-589.e3, doi: 10.1016/j.jpeds.2007.12.018.
(Continued)

*Primary Examiner* — Carl H Layno
*Assistant Examiner* — Jon Eric C Morales
(74) *Attorney, Agent, or Firm* — Saliwanchik, Lloyd & Eisenschenk

(57) ABSTRACT

Provided is a Coupled Domain Sensor (CDS) that can be used to, for example, evaluate hydration and occlusion of blood in patients with edema using electrical and optical measurements. Advantageously, the CDS provides a quicker, more effective and accurate way of monitoring this medical condition.

20 Claims, 7 Drawing Sheets

Normalized Oxygen Saturation of Hemoglobin in the Finger

(51) Int. Cl.
    *A61B 5/145*     (2006.01)
    *A61B 5/026*     (2006.01)
    *A61B 5/053*     (2006.01)
    *A61B 5/0205*     (2006.01)
    *A61B 5/11*     (2006.01)

(52) U.S. Cl.
    CPC ............ *A61B 5/0537* (2013.01); *A61B 5/443* (2013.01); *A61B 5/0022* (2013.01); *A61B 5/1123* (2013.01); *A61B 5/14542* (2013.01); *A61B 5/6824* (2013.01); *A61B 5/6825* (2013.01); *A61B 5/6826* (2013.01); *A61B 5/6829* (2013.01); *A61B 2560/0214* (2013.01); *A61B 2560/0475* (2013.01); *A61B 2562/0219* (2013.01); *A61B 2562/0271* (2013.01)

(58) Field of Classification Search
    USPC ...................................... 600/373, 391; 607/3
    See application file for complete search history.

(56) References Cited

U.S. PATENT DOCUMENTS

2015/0335288 A1* 11/2015 Toth ..................... A61B 5/6833
                                                                                           600/373
2015/0374256 A1* 12/2015 Skrabal ................ A61B 5/0408
                                                                                          600/301

OTHER PUBLICATIONS

Cox, N.H., "Oedema as a Risk Factor for Multiple Episodes of Cellulitis/Erysipelas of the Lower Leg: A Series With Community Follow-Up," *Clinical and Laboratory Investigations,* Apr. 2006, 155:947-950, doi: 10.1111/j.1365-2133.2006.07419.x.

Daniel-Spiegel, E. et al., "Hydrops Fetalis: An Unusual Prenatal Presentation of Hereditary Congenital Lymphedema." *Prenatal Diagnosis,* Oct. 2005, 25:1015-1018, doi: 10.1002/pd.1237.

Finegold, D.N. et al., "Connexin 47 Mutations Increase Risk for Secondary Lymphedema Following Breast Cancer Treatment." *Clin. Cancer Res.,* Apr. 2012, 18(8):2382-2390, doi: 10.1158/1078-0432. CCR-11-2303.

Greene, A.K., Schook, C.C., "Primary Lymphedema: Definition of Onset Based on Developmental Age." Plastic and Reconstructive Surgery, Jan. 2012, 129:221e-222e, doi: 10.1097/PRS. 0b013e3182365c91.

Lewis, J.M., Wald, E.R., "*Lymphedema Praecox.*" The Journal of Pediatrics, May 1984, 104(5):641-648.

Miaskowski, C. et al., "Lymphatic and Angiogenic Candidate Genes Predict the Development of Secondary Lymphedema Following Breast Cancer Surgery." *Plos One,* Apr. 2013, 8(4):1-20, doi: 10.1371/journal.pone.0060164.

Mukamel, S., Abramavicius, D., "Many-Body Approaches for Simulating Coherent Nonlinear Spectroscopies of Electronic and Vibrational Excitons." *Chem. Rev.,* Apr. 2004, 104(4):2073-2098, doi: 10.1021/cr020681b.

Murdaca, G. et al., "Current Views on Diagnostic Approach and Treatment of Lymphedema." *The American Journal of Medicine,* Feb. 2012, 125(2):134-140, doi: 10.1016/j.amjmed.2011.06.032.

Oremus, M. et al., "Systematic Review: Conservative Treatments for Secondary Lymphedema." *BMC Cancer,* Jan. 2012, 12(6):1-15, doi: 10.1186/1471-2407-12-6.

Rizzo, C. et al., "Lymphedema Praecox." *Dermatology Online Journal,* Aug. 2009, 15(8):7.

Rockson, S.G., "Lymphedema." *American Journal of Medicine,* Mar. 2001, 110:288-295, doi: 10.1016/S0002-9343(00)00727-0.

Wheeler, E.S. et al., "Familial Lymphedema Praecox: Meige's Disease." *Plastic and Reconstructive Surgery,* Mar. 1981, 67(3):Abstract.

Woo, P.C.Y. et al., "Cellulitis Complicating Lymphoedema." *Eur. J. Clin. Microbiol. Infect. Dis.,* 2000, 19:294-297.

Zeldenryk, L.M. et al., "The Emerging Story of Disability Associated with Lymphatic Filariasis: A Critical Review." *PLoS Negl. Trop. Dis.,* Dec. 2011, 5(12):1-8, doi: 10.1371/journal.pntd. 0001366.

Zhang, W.M. et al., "Multidimensional Femtosecond Correlation Spectroscopies of Electronic and Vibrational Excitons." *Journal of Chemical Physics,* Mar. 1999, 110(11):5011-5028, doi: 10.1063/1. 478400.

Zimmermann, A. et al., "Efficacy of Manual Lymphatic Drainage in Preventing Secondary Lymphedema After Breast Cancer Surgery." *Lymphology,* Sep. 2012, 45(3):103-112.

\* cited by examiner

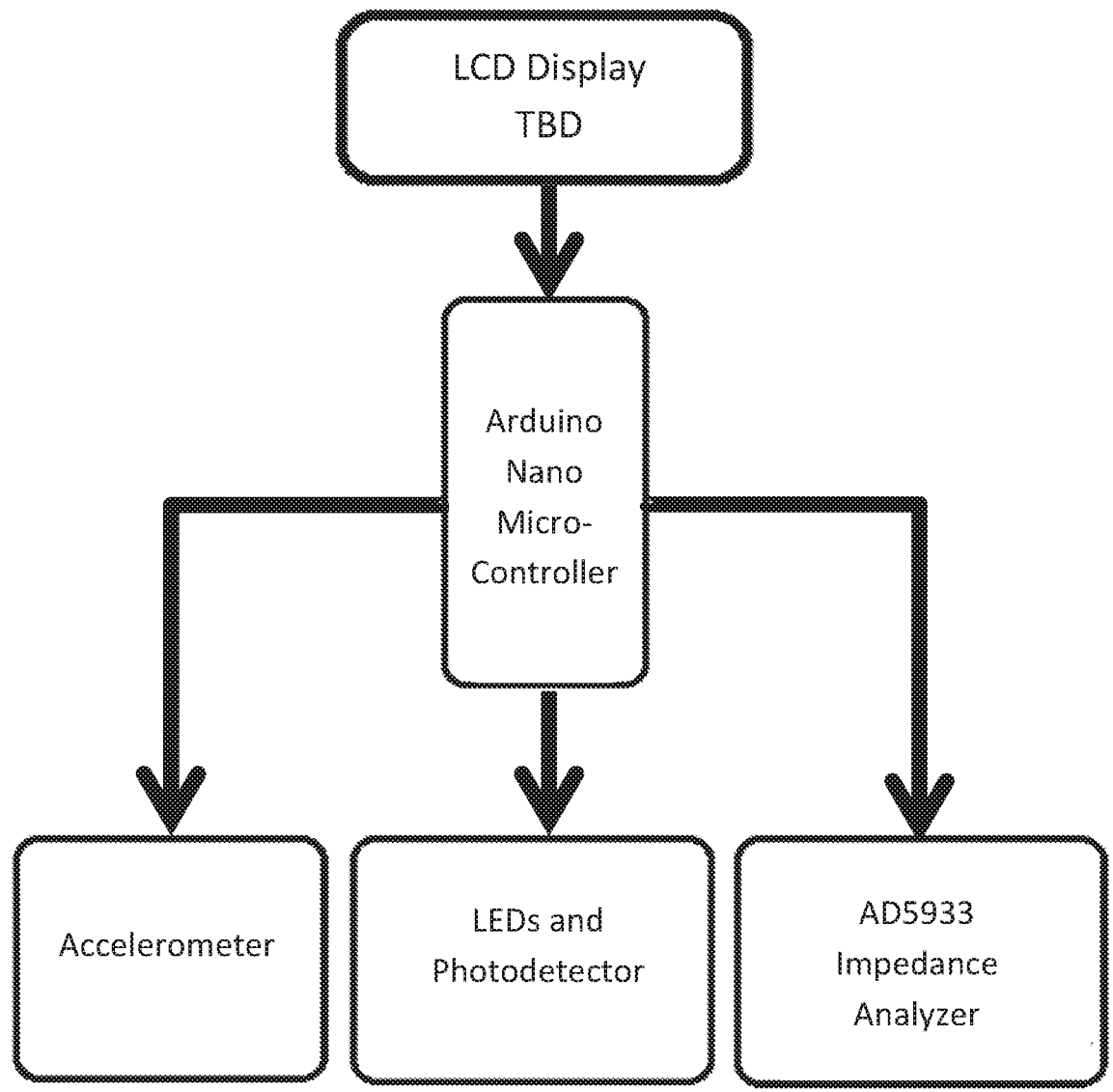

MATERIALS AND METHODS FOR DETECTING AND MONITORING EDEMA AND RELATED CONDITIONS

CROSS-REFERENCE TO A RELATED APPLICATION

This application claims the benefit of U.S. provisional application Ser. No. 62/162,520, filed May 15, 2015, which is incorporated herein by reference in its entirety.

BACKGROUND OF THE INVENTION

Edema is an abnormal accumulation of fluid in the interstitium, located beneath the skin and in the cavities of the body. Clinically, edema is manifest as swelling. The amount of interstitial fluid is determined by the balance of fluid homeostasis; increased secretion of fluid into the interstitium, or the impaired removal of the fluid can cause edema. The more the fluid accumulates, the more the tissue swells, resulting in decreased blood flow in the blood vessels of the dermis. Although edema can occur anywhere in the body, it is most commonly seen in the ankles, feet, and legs.

The skin is the largest organ in the body and it acts as the first line of defense against environmental factors. The skin has multiple layers. The stratum corneum is the outermost layer of the skin and forms part of the epidermis. The dermis, which is underneath the epidermis, is mainly composed of capillaries and lymph vessels. Skin thickness varies. The epidermis is only 0.05 mm thick on the eyelids, but is 1.5 mm thick on the palms and the soles of the feet. Thickness of the dermis varies from 1.5 mm to 4 mm.

Normally the hydrostatic pressure of a capillary is about 35 mmHg in the arteriole and 18 mmHg in the venule [1]. The normal osmotic pressure of a capillary is 25 mmHg for both arterioles and venules [1]. Disruption of these pressures alters the osmotic balance, consequently causing edema. Other common causes of edema include decreased plasma proteins, increased capillary permeability, and blockage of the lymphatic system.

Lymphedema is an abnormal accumulation of lymphatic fluid in the interstitial tissue that causes swelling, most often in the arm(s) and/or leg(s) and occasionally in other parts of the body due to a compromised lymphatic system. The lymphatic system is composed of a network of lymph vessels (some of which are found in the dermis), tissues, and organs that transport lymph fluid throughout the whole body. It also collects and filters the interstitial fluid of the body. In addition, the lymphatic system prepares the body for when it is time to fight an infection or disease.

Proper function of the lymphatic system is critical for a healthy individual. Normally, lymph is transported throughout the body and delivered back to the bloodstream; however, when the lymphatic system is blocked or damaged, the fluid is not drained from the tissues. As a consequence, an abnormal accumulation of extracellular fluid occurs, leading to excessive swelling of the tissue. As the fluid accumulation increases and the tissue swells, the pressure build-up in the affected limb causes a decrease in blood flow.

There are two types of lymphedema: primary or secondary. Primary lymphedema occurs when a person is born with an abnormal lymphatic system. Secondary lymphedema occurs when lymph vessels are damaged or lymph nodes are removed due to certain factors, such as radiation, burns, tumors, infections, and/or trauma. In the United States, the most common cause of secondary lymphedema is breast cancer surgery combined with radiation therapy [10-12]. Surgery and/or treatment for prostate, colon and testicular cancers may result in secondary lymphedema, particularly where lymph nodes have been removed or damaged.

When a patient has chronic lymphedema, some of the most prominent skin changes that arise as the condition progresses include papillomatosis, lymphangiectasia, and hyperkeratosis. There are certain inflammatory conditions that may contribute to lymphedema development, including sarcoidosis, rheumatoid arthritis, and psoriasis. Some cases of patients with acne vulgaris and rosacea have developed lymphedema in the face. Certain patients who have suffered from a form of trauma, such as varicose vein surgery and radiotherapy, have also developed lymphedema due to the damage caused to their lymphatic system. Finally, patients with venous disease are predisposed to lymphedema because of the increased capillary filtration and the incompetence of the lymphatic system When the impairment becomes so great that the lymphatic fluid exceeds the lymphatic transport capacity, an abnormal amount of protein-rich fluid collects in the tissues of the affected area. Left untreated, this stagnant, protein-rich fluid not only causes tissue channels to increase in size and number, but also reduces oxygen availability in the transport system, interferes with wound healing, and provides a culture medium for bacteria that can result in lymphangitis (infection). Symptoms may include severe fatigue, a heavy swollen limb or localized fluid accumulation in other body areas, deformity ("elephantiasis"), discoloration of the skin overlying the lymphedema, recurrent episodes of cellulitis, and in severe cases, skin ulcers and infections.

Lymphedema may also result in psychological distress. The normal, daily-living lifestyle can become severely limited. A treatment for lymphedema is called Complete Decongestive Therapy, which may include manual lymphatic drainage, compression therapy, short stretch compression bandaging, therapeutic exercise, and skin care.

Lymphedema affects approximately 140 million people in the world and approximately 5 million people in the United States. In addition, out of the 2.5 million breast cancer survivors, lymphedema occurs in 40% of those patients because cancer treatment damages the patients' lymphatic system. Currently, there is no technology that offers patients an understanding of what actions may aggravate their conditions or that aids in managing lymphedema.

Therefore, the ability to gain insights into, and/or monitor, this disease and its progression are of great interest.

BRIEF SUMMARY OF THE INVENTION

The subject invention provides a Coupled Domain Sensor (CDS) that can be used to quantify and/or monitor hydration and occlusion of blood in patients with edema using electrical and optical measurements. Advantageously, the CDS provides a quicker, more effective and accurate way of monitoring this medical condition.

The subject invention also provides a device comprising a CDS to clinically quantify and/or monitor hydration and occlusion of blood in patients with edema, preferably lymphedema, and lymphatic disease. The subject invention further provides methods of using such CDS devices.

In one embodiment, the CDS of the subject invention couples electrical signals with optical signals through at least one electrical sensor and at least one optical sensor. The electrical sensor measures the skin hydration using bioelectrical impedance analysis while the optical sensor measures the occlusion of blood flow via optical detection.

In one embodiment, the CDS device of the subject invention comprises at least one electrical component and at least one optical component, wherein the electrical component comprises an electrical sensor comprising at least two electrodes and an impedance analyzer, and wherein the optical component comprises an optical sensor that comprises a light source and a photodetector. The CDS device can further comprise an accelerometer for motion detection and at least one microcontroller or nano microcontroller.

In a further embodiment, the impedance analyzer of the electrical sensor comprises an impedance analyzer evaluation board or an impedance analyzer evaluation chip.

The light source of the optical sensor can be, for example, an LED or laser. The photodetector can be, for example, a spectrometer or camera.

The method of the subject invention advantageously integrates two technologies (optical and electrical) to better quantify and monitor patients with edema. The optical technology is mainly used to measure the occlusion of blood flow while the electrical technology measures fluid build-up in the skin using bioelectrical impedance analysis.

In a specific embodiment, the subject invention utilizes orthogonal sensing of (a) personalized algorithm for human body movements, and (b) surface and sub-surface properties of tissue (e.g., skin) to correlate movements that accelerate or ameliorate edema in patients. The body movements can be recorded with standard accelerometers and correlated with data from, for example, miniature, wearable multimode sensors capable of tracking water content, blood flow oxygenation and deoxygenation.

Advantageously, the device of the subject invention can be non-invasive, portable, and may also be wearable. In certain embodiments, the measurements can be collected in an affected limb.

In one embodiment, the subject invention provides a method for measuring the skin hydration, and for monitoring such condition in a subject. The method can comprise attaching the CDS device to a desired tissue or body part of the subject, measuring the skin hydration, and/or monitoring such condition with such device. Preferably, the body part is a limb, hand, foot, finger, toe, wrist or ankle. The subject can be a human or other animal.

In one embodiment, the subject invention provides a method for measuring the occlusion of blood, and for monitoring such condition in a subject, comprising attaching the CDS device to a desired tissue or body part of a subject, measuring the occlusion of blood, and/or monitoring such condition. Preferably, the body part is a limb, hand, foot, finger, toe, wrist or ankle. The subject can be a human or other animal.

In one embodiment, the subject invention provides a method for measuring the skin hydration and occlusion of blood in a subject, preferably a human, and for monitoring such conditions, comprising attaching the CDS device to a desired tissue or body part of a subject, measuring the skin hydration and occlusion of blood, and/or monitoring such conditions with such device. Preferably, the body part is a limb, hand, foot, finger, toe, wrist or ankle.

Advantageously, the device of the subject invention can provide personalized collection of data in order to predict certain conditions and aid in the prevention of fluid build-up. In certain embodiments the sensor provides insights into what actions may aggravate a patient's condition.

The subject invention further provides a method for predicting the fluid build-up and occlusion of blood in a subject, preferably a human patient, and for diagnosing edema, preferably lymphedema, comprising a) attaching the CDS device to a desired tissue or body part of a subject, b) measuring the skin hydration and occlusion of blood and/or monitoring such conditions with such device, c) comparing the measured levels of skin hydration and occlusion of blood to a control or reference sample that is, for example, an unaffected, healthy tissue or body part, and d) determining the likelihood of fluid build-up and occlusion of blood flow based on the comparison. The subject invention also provides a method for diagnosing the edema, preferably lymphedema, in a subject using the CDS device.

The subject invention provides patients and physicians with better long term monitoring that can assist in the treatment of this condition, lower health care cost and empower patients with the knowledge to better their wellness and quality of life.

BRIEF DESCRIPTION OF THE DRAWINGS

FIG. 6 shows Device 2.

DETAILED DESCRIPTION OF THE INVENTION

Figure 1A:
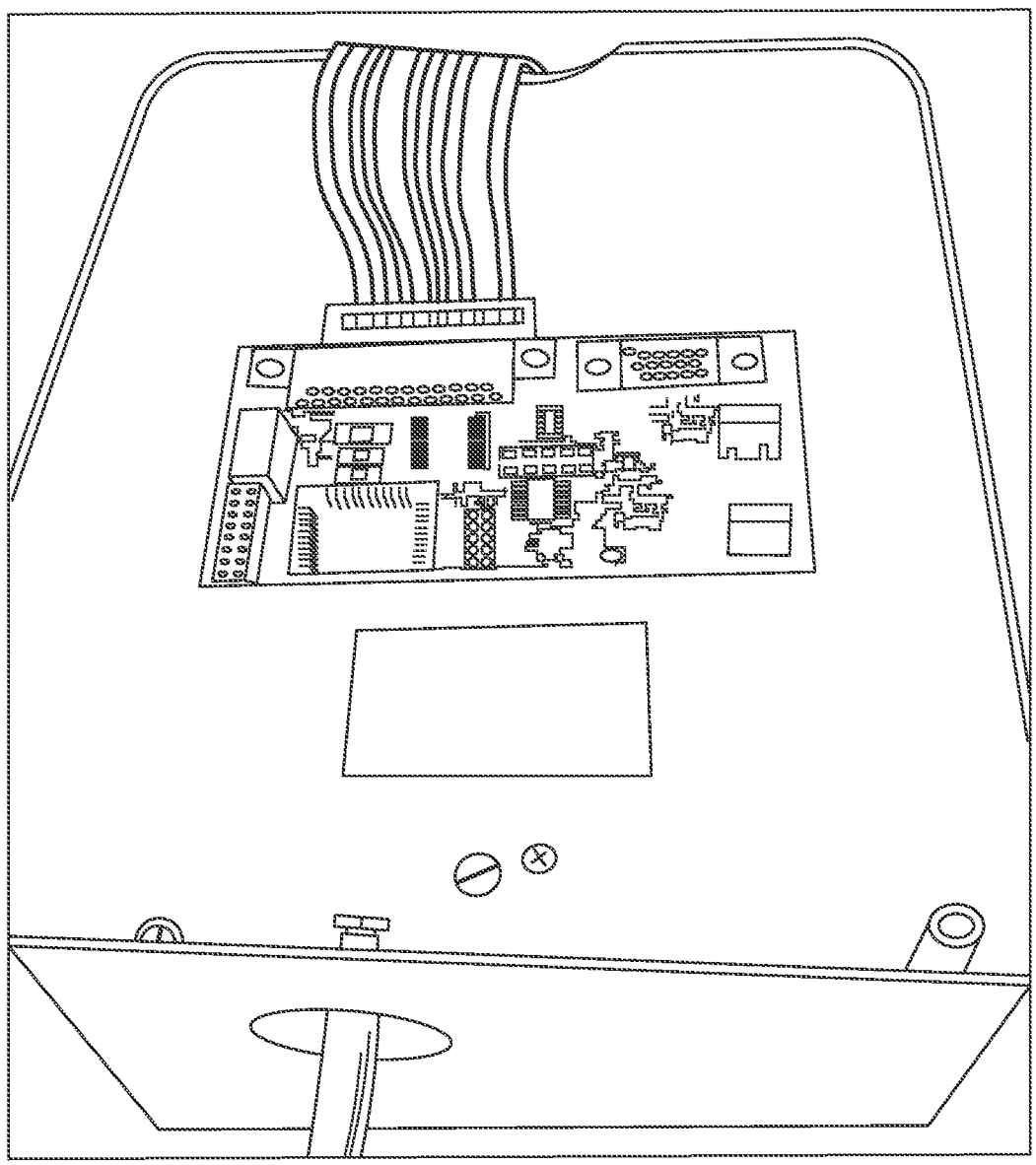
FIG. 1A shows the Ocean Optics Spectrometer.

The subject invention provides a Coupled Domain Sensor (CDS) that evaluates skin hydration and occlusion of blood in patients with edema using electrical and optical measurements. Advantageously, the CDS of the subject invention provides a quicker, more effective and accurate way of monitoring this medical condition.

The subject invention also provides devices comprising a CDS for clinically evaluating skin hydration and occlusion of blood in a subject with edema, preferably lymphedema and/or lymphatic disease. The subject invention further provides methods for quantification of skin hydration and occlusion of blood in a subject with edema using the CDS device. The subject can be an animal, such as a human.

The CDS of the subject invention couples electrical signals with optical signals through at least one electrical sensor and at least one optical sensor. The electrical sensor measures skin hydration using bioelectrical impedance, while the optical sensor measures the occlusion of blood flow.

A further advantage of one embodiment of the coupled domain sensor is that it measures localized water retention, which facilitates differentiating this condition from body hydration.

Advantageously, the subject invention integrates two technologies (optical and electrical) into a single device to better quantify and monitor patients with lymphedema. The optical component of the device measures occlusion of blood flow. The electrical component of the device measures fluid build-up in the skin using bioelectrical impedance analysis.

In one embodiment, the CDS device comprises at least one electrical component and at least one optical component, wherein the electrical component comprises at least two electrodes, preferably four electrodes, and an impedance analyzer, and wherein the optical component comprises a light source and a photodetector. The device can also comprise an accelerometer for motion detection and at least one microcontroller or nano microcontroller.

In a further embodiment, the impedance analyzer of the electrical sensor comprises an impedance analyzer evaluation board or an impedance analyzer evaluation chip. The light source of the optical sensor can comprise, for example, an LED or laser. The photodetector can comprise a spectrometer or camera.

In one embodiment, the electrical component of the device comprises functional parts to take physiological measurements, transmit data and receive commands from a microcontroller. The electrical component of the device can also comprise circuitries such as activity circuitry, electronics circuitry and impedance circuitry. The electronics circuitry may further comprise a real-time clock and frequency-generator circuitry. In certain embodiments, the electronics circuitry may comprise a temperature sensor for measuring the temperature of the patient as changes in the skin temperature may affect impedance and/or hydration measurements.

In one embodiment, the CDS measures tissue water content with an electrical sensor and impedance circuitry by applying a suitable electrical current flowing through the desired tissue or body part. The impedance circuitry is electrically connected to electrodes. At least one reference electrode and at least one measurement electrode can be attached to the desired tissue or body part. Depending on the amount of water in the tissue or body part, current flow will be affected, and the resistance to the current flow is then measured. The applied current can be a DC current or an alternating current (AC). The impedance analyzer evaluation board or an impedance analyzer evaluation chip provides an impedance measurement ranging from 10Ω to 100 MΩ, preferably from 1 kO to 10 MO.

The bioelectrical impedance reflects how much water is in the tissue, affected body part, or entire body, which also allows for calculation of the amount of body fat. Tissues with high conductivity will contain large quantities of electrolytes and fluids, which allow the current to flow without much resistance, whereas tissues with low conductivity, such as fat and bones, generate high resistance to the flowing current.

In one embodiment, the current is an alternating current, preferably a low level alternating current ranging from 1 μA to 2000 μA, preferably from 10 μA to 1000 μA, more preferably from 50 μA to 1000 μA, and most preferably, from 200 μA to 800 μA.

The CDS can send an alternating current through the tissue or affected body part at a single frequency or at several different frequencies. The single frequency bioelectrical impedance analysis can be performed using a single frequency ranging from 0.5 kHz to 2000 kHz, preferably from 1 kHz to 500 kHz, more preferably 50 kHz. The multifrequency bioelectrical impedance analysis measures the water content by quantifying the bioelectrical impedance at different frequencies ranging from 0.5 kHz to 1000 kHz, preferably from 1 kHz to 500 kHz. For example, quantification of the amount of extracellular water (ECW) can be performed at low frequencies, such as 1 kHz or 5 kHz while total body water can be quantified at higher frequencies, such as 100 kHz, 200 kHz, or 500 kHz.

When measuring skin impedance, surface electrodes are able to convert the ionic current that is found in the body into electronic current. The junction between the electrode and the skin arises from the need of directing electrical currents into or away from the body. Additionally, the impedance level also depends on the size of the electrode. For instance, the impedance of the surface electrode/skin junction decreases when the electrode surface area is bigger. Similarly, when the surface area of the electrodes is small, then the impedance value would be much higher. Therefore, it is important to keep these factors in mind when designing electrodes for collecting measurements in the skin.

The CDS can also comprise a circuitry to minimize the errors in the measurement of impedance and increase the signal to noise ratio. These errors may be caused by many factors including, but not limiting to, the junction potential raised between the electrodes and the skin, the electrical noise from the sensors and environment, time delays of the circuitry, and/or time delays of the measurement.

The CDS according to the subject invention may measure body water content such as ECW using single frequency bioelectrical impedance analysis (SF-BIA), multifrequency bioelectrical impedance analysis (MF-BIA), BIS, and bioelectrical impedance analysis vectors.

In a specific embodiment, the bioelectrical impedance may also be used to measure the skin blood flow.

In one embodiment, the optical component of the CDS according to the current invention comprises an optical sensor that includes a light source, such as an LED or a laser, and a photodetector or optical detector such as a spectrometer or a camera. Preferably, the photodetector is capable of separately measuring infrared, full spectrum, or human visible light.

The light source shines light on the desired tissue or body part while the photodetector measures the light absorption of the tissue or body part. Light absorption via tissue spectroscopy provides a good measurement of the chemical composition of the tissue.

In one embodiment, the light source emits light that exhibits various depths of optical penetration. The depth also depends on the wavelength used. For example, the infrared and red visible wavelengths are able to penetrate deeper in the skin than wavelengths such as the violet visible or the ultraviolet. Moreover, this depth may also depend on the separation distance between the light source and the optical detector. The optical component according to the current invention comprises the light source and the optical detector with a fixed or variable separation distance that is suitable for any part of the body including torso, limbs, fingers, and toes. In a preferred embodiment, the separation distance between the light source and the optical detector ranges from 0.8 mm to 3.0 mm.

In a further embodiment, a low power laser beam penetrates the skin, so the light that strikes and moves blood cells is reflected with a frequency shift, which allows determining the relative blood flow.

In certain embodiments, the light that enters the skin or tissue may be absorbed by chromophores in a wavelength-dependent manner. Alternately, the light that enters the skin or tissue may change direction of propagation during a scattering event. Following a sufficient number of scattering events, the light that has not been absorbed may find its way out of the skin or tissue, which can be captured by the optical detector. The information collected may be further analyzed by the optical sensor to obtain the tissue optical properties. In a preferred embodiment, the light source emits light in the wavelength range of 400-1000 nm.

In one embodiment, the optical component of the CDS provides a continuous measurement of the absorbance spectrum of the desired tissue or affected body part. The optical component of the CDS also provides measurement of the absorbance spectrum of hemoglobin in an oxygen-loaded (oxy-hemoglobin) and/or -unloaded (deoxy-hemoglobin) form in the desired tissue or body part. The CDS is also able to utilize an algorithm to convert the absorbance to the concentrations of oxy-hemoglobin and deoxy-hemoglobin.

Figure 3:
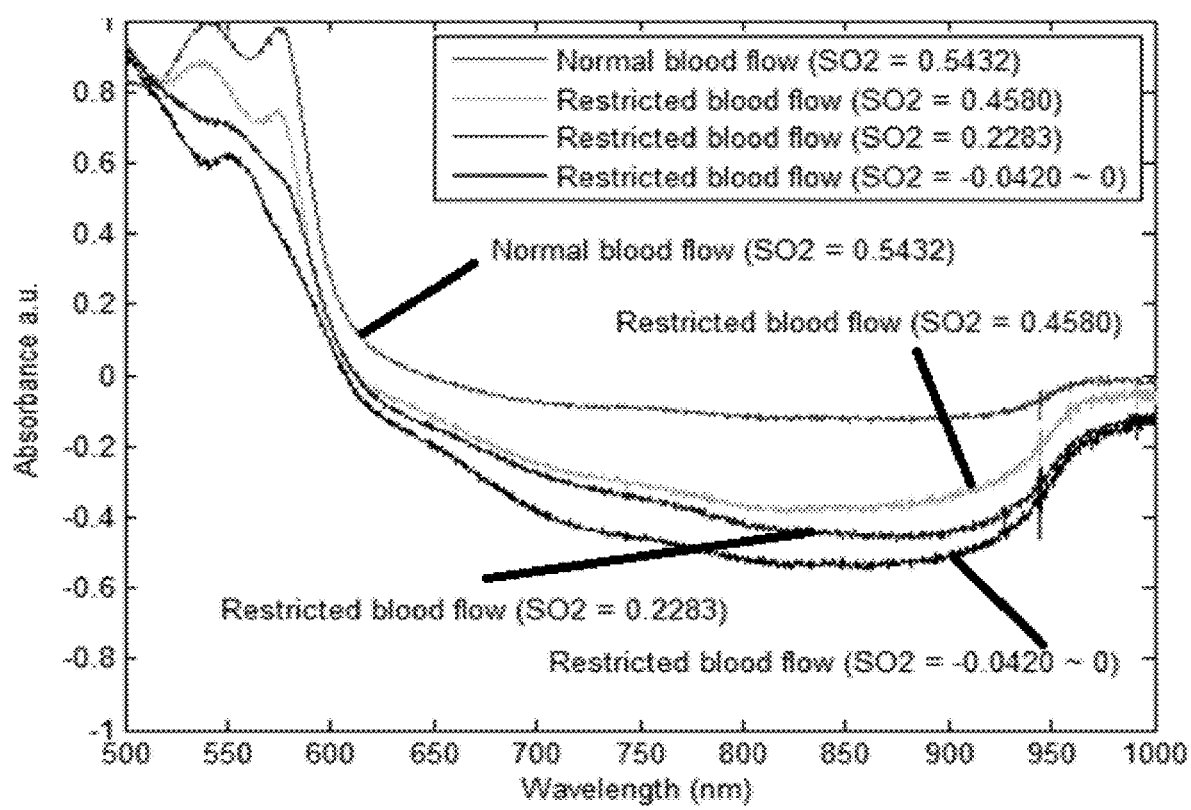
FIG. 3 shows the absorption spectrum of hemoglobin measured in the finger under normal condition and conditions with restricted blood flow.

In one embodiment, the CDS device measures the oxygen saturation of hemoglobin (occlusion of blood) in the desired tissue or body part such as, for example, the finger (See FIG. 3). The light used for oxygen saturation of hemoglobin has a wavelength ranging from 400 nm to 700 nm. Preferably, the maximum absorption of skin hemoglobin occurs at the wavelength between 560 nm and 580 nm. The measurement may be made at an individual time point or in a continuous manner.

In a specific embodiment, the optical component of the CDS may also be used to measure the water content in the desired tissue (e.g., skin) by absorption analysis. The light used for hydration measurement has a wavelength ranging from 700 nm to 1000 nm. Preferably, the maximum absorption of skin hydration occurs at around 970 nm. The optical component of the CDS may further function as an optical spectroscope, for example, for measurement of the amount of water and hemoglobin.

In one embodiment, the current invention provides a CDS device for determining the skin hydration and occlusion of blood flow in patients with edema, preferably lymphedema. The measurements of skin water content and saturation of hemoglobin from the desired tissue or body part with edema may be further compared with a control or reference that is obtained from an unaffected, healthy tissue or body part. The CDS device may also be used to establish a baseline of the measurement from the patient and monitor it over time to monitor the progression of the condition in the patient. Thus, the CDS device also provides a means to predict and diagnose the condition of edema. In a further embodiment, the CDS device can also be used to predict and prevent the accumulation of water in the skin as well as the occlusion of blood.

In one embodiment, by acquiring at various wavelengths, the CDS device may be used to generate a hemoglobin absorbance map of the desired tissue or body part. The CDS device may also be used to generate a water absorbance map of the desired tissue or body part. In a further embodiment, the CDS device may be able to generate a 3D feature map of the edematous skin.

In one embodiment, the CDS device provides measurements of water content and occlusion of blood from a desired tissue or body part of a subject. The desired body part is preferably a limb, hand, foot, finger, toe, wrist or ankle. The subject is preferably a human.

In one embodiment, the device further comprises an activity sensor such as an accelerometer. The accelerometer can comprise at least one of a piezo-electric accelerometer, capacitive accelerometer or electro-mechanical accelerometer. The accelerometer may also comprise a 3-axis accelerometer to measure at least one of an inclination, a position, an orientation, or acceleration of the subject in three dimensions.

In a specific embodiment, the subject invention utilizes orthogonal sensing of (a) a personalized algorithm for human body movements, and (b) surface and sub-surface properties of tissue (e.g., skin) to correlate movements that accelerate edema in patients. The body movements can be recorded with standard accelerometers and correlated with data from miniature, wearable multimode sensors capable of tracking water content, blood flow oxygenation and deoxygentation-electrically and optically.

In some embodiments, the CDS device may further comprise a battery, memory, wireless communication capabilities, filters for various light spectra and algorithms for data analysis. In a further embodiment, the battery may be a rechargeable battery that can be plugged to a power outlet. The battery may also be a solar powered battery. The battery also provides a safe protection for the CDS device in case of a power outage. In another embodiment, the CDS device comprises memory for data collection and storage including temporary data storage and permanent storage. The memory may be expandable or removable.

In one embodiment, the CDS device may further comprise wireless communication capabilities. The CDS device may transfer data to/between other CDS device, computers, tablets, smartphones, medical devices or platforms through a wire connection or wireless communication. The CDS device can also be synchronized to other CDS devices, computers, tablets, smartphones, medical devices or platforms.

In one embodiment, the CDS device is used for measuring impedance of a tissue, or a body part of a subject. The body part is preferably a limb, hand, foot, finger, toe, wrist or ankle.

In one embodiment, the device may be a stand-alone device, a compatible device to be added on other medical devices, or a small wearable device that can be worn/attached to the desired tissue or body part. In a specific embodiment, the device may be connected to a spectrometer for measurements.

In one embodiment, the subject invention provides a method for measuring the skin hydration, and for monitoring such condition in a subject, comprising attaching the CDS device to a desired tissue or body part of the subject, measuring the skin hydration, and/or monitoring such condition with such device. Preferably, the body part is a limb, hand, foot, finger, toe, wrist or ankle. The subject can be a human or other animal.

In one embodiment, the subject invention provides a method for measuring the occlusion of blood, and for monitoring such condition in a subject, comprising attaching the CDS device to a desired tissue or body part of a subject, measuring the occlusion of blood, and/or monitoring such condition. Preferably, the body part is a limb, hand, foot, finger, toe, wrist or ankle. The subject can be a human or other animal.

In one embodiment, the subject invention provides a method for measuring the skin hydration and occlusion of blood in a subject, preferably a human, and for monitoring such condition, comprising attaching the CDS device to a desired tissue or body part of a subject, measuring the skin hydration and occlusion of blood, and/or monitoring such conditions with such device. Preferably, the body part is a limb, hand, foot, finger, toe, wrist or ankle.

In one embodiment, the device can be worn or attached to a desired tissue or body part in many ways including, for example, by pressure, with an adhesive tape/patch, a constant-force spring, a screw-in microneedle electrode, a pinch onto roll of skin, or transcutaneous anchoring. In another embodiment, the device may be a flexible epidermal electronics in which all sensors are mounted on elastomeric and ultrathin sheets.

In one embodiment, the CDS device is a wearable or a swappable device to take a selected measurement (e.g., skin hydration and occlusion of blood) and/or monitor measured data. Such device may be a wearable wristband, on the limb, or on the finger. FIG. 1B shows the source and detector worn on the finger. Such device may comprise one or more other sensors such as a heart rate monitor, a blood pressure sensor, a pulse oximeter, or a gyroscope and can be used to take selected measurements.

In one embodiment, the subject invention provides a method for predicting the fluid build-up and occlusion of blood in a subject, preferably, a human patient, comprising a) attaching the CDS device to a desired tissue or body part of a subject, b) measuring the skin hydration and occlusion of blood, c) comparing the measured levels of skin hydration and occlusion of blood to a control or reference sample that is an unaffected, healthy tissue or body part, and d) determining the likelihood of fluid build-up and occlusion of blood flow based on the comparison, wherein the level of fluid build-up having at least 5% increase compared to the reference or control indicates the likelihood of fluid build-up, and wherein the saturation level of hemoglobin having at least 5% decrease compared to the reference or control indicates the likelihood of occlusion of blood flow. Preferably, the level of fluid build-up and the saturation of hemoglobin having 10%, 15%, 20%, 25%, 30%, 35%, 40%, 45%, or 50% difference compared to the reference or control indicates the likelihood of fluid build-up, and occlusion of blood flow.

In a further embodiment, the method according to the subject invention can involve using the CDS device to establish a baseline of the measurement from the patient, for example, before taking actual measurements, and monitor it over time to obtain the progression of the condition in the patient In one embodiment, the subject invention provides a method for diagnosing the edema, preferably, lymphedema in a subject, preferably, a human patient, comprising a) attaching the CDS device to a desired tissue or body part of a subject, b) measuring the skin hydration and occlusion of blood, c) comparing the measured levels of skin hydration and occlusion of blood to a control or reference sample that is an unaffected, healthy tissue or body part, and d) diagnosing the fluid build-up and occlusion of blood flow based on the comparison, wherein the level of fluid build-up having at least 5% increase compared to the reference or control indicates the likelihood of fluid build-up, and wherein the saturation level of hemoglobin having at least 5% decrease compared to the reference or control indicates the likelihood of occlusion of blood flow. Preferably, the level of fluid build-up and the saturation of hemoglobin having 10%, 15%, 20%, 25%, 30%, 35%, 40%, 45%, or 50% difference compared to the reference or control indicates the development of edema, preferably, lymphedema.

Advantageously, in certain embodiments, the device of the subject invention provides personalized collection of data in order to predict certain conditions and aid in the prevention of fluid build-up. This sensor provides insights into what actions may aggravate the patient's condition.

In certain embodiments, the device according to the subject invention may be used in combination with an additional method for measuring the skin hydration and occlusion of blood flow. Such methods include, but are not limited to, water displacement measurement, tape measurement, disk model method, Frustrum Method (Sitzia's Method), perometry, and medical imaging approaches (e.g., CT, MRI and ultrasound).

The water displacement method has been the long used 'gold standard' for lymphedema detection throughout the years. It allows assessing limb volume in a very simple way; however, this technique is now rarely used because of the inconvenience that it presents for the patients. The 'gold standard' consists of measuring the body part by submerging it in a large cylindrical container full of water. Then, the displaced water is measured, providing an estimate of the body part volume. This approach cannot provide accurate information about the exact part/location of a swollen area on the limb. In addition to being inconvenient for patients, this technique is laborious and difficult to use in a clinical setting due to water spillage.

Tape measurement is a common type of measure of volume in lymphedema patients. It can be gathered at defined intervals using a tape meter. The collected values can then be used with geometric formulas, in order to calculate the total volume. Although this is a widely used approach, the measurement precision is user dependent.

The disk model method is a common technique consisting dividing the limb into 10 disks. Each of these disks is given a size of 5 cm. The next step is to calculate the volume of each of the 10 disks and add them. In the arm, the measurements are usually collected at the hand, at the wrist, and below and above the lateral epicondyle. This technique may be easy, inexpensive, and reliable. However, when it comes to limb circumference measurements, it is not possible to obtain an accurate estimate of the hand's volume because of its asymmetrical shape.

The Frustrum method consists in implementing surface circumference measurements at 4 cm or 8 cm intervals, along with a mathematical formula (equation (1)) derived from a frustrum's formula, which allows determining the volume of the arm.

$$V = L/4\pi(c1c2 + c2c3 + c3c4 + \ldots c13c14) \quad (1)$$

where L is the length of the interval (4 cm or 8 cm) and c is the circumference of the arm. This method is inexpensive and hardly inconvenient for the patient; nevertheless accuracy and precision of the measurement is an issue, just like for the previously-described methodologies.

Perometry is a technique where an infrared optical electronic scanner is used to compute the volume of a body part. Perometry has been verified to be accurate when compared to the "gold standard" of water displacement and a great tool lymphedema research. This technique can only be accurate if the affected body area is positioned consistently for every measurement.

Medical imaging approaches including CT, MRI and ultrasound. CT imaging has shown to be highly sensitive and specific for lymphedema diagnosis. MRI can provide a sensitive diagnosis of lymphedema with detailed soft tissue architecture, without radiation exposure. These techniques can provide accurate information about the presence of excessive interstitial fluids when the information is compared with patient history, physical examination and other imaging tests. However, these techniques are limited to the clinical lab set-up and not convenient for continuous monitoring of lymphedema disease/treatment progression. Radio-labelled particles are injected under the area of the skin to be imagined during lymphoscintigraphy. Due to radio-labelled enhance imaging, this approach can provide accurate diagnosis of irregularities in lymphatic flows, lymph uptakes and treatment response. With advances in optical imaging, a 3D surface imaging approach can provide detailed information of the noncontact volume measurement with higher speed, accuracy, and ease of use.

The subject invention provides patients and physicians with better long term monitoring that will assist in the treatment of this condition, will lower health care cost and will empower patients with the knowledge to better wellness and quality of life.

In some embodiments, the subject invention relates to patient monitoring. Although embodiments make specific reference to monitoring impedance with an adherent patch and optical absorbance, the sensors, system methods and devices described herein may be applicable to many situations in which physiological monitoring with impedance measurement and optical absorbance are used, for example, physiological monitoring with implantable devices.

In some embodiments, the device may continuously monitor patients' physiological or medical parameters, communicate wirelessly and provide alerts when necessary. The physiological parameters may be selected from: bioimpedance, respiration, respiration rate variability, heart rate, heart rhythm, blood pressure, activity, posture, wake/sleep, temperature, weight, hydration and blood oxygen level. The device may further perform the functions selected from initiation, programming, measuring, storing, analyzing, communicating, predicting and displaying.

In one embodiment, the CDS device may comprise a component including a communication module configured to receive display information and performing commands from at least one external device, and at least one display area. Preferably, the display is a LED display. The external device may include another CDS device, a computer, a tablet, a smartphone, or an oscilloscope. External commands from these devices may be programmed by general or medical Apps or software such as LabView. The display area of the CDS device may comprise a main display area and a sub-display area, wherein the main display area is for the display information including selected measurements, and physiological parameters, and wherein the sub-display area is for other information including patient identification, time, external commands and so forth.

The following patents of interest are incorporated herein, by reference, in their entireties: U.S. Pat. Nos. 8,523,794; 8,412,317; 8,374,688; 8,660,629; 8,548,580; and 8,652,042.

It should be understood that the examples and embodiments described herein are for illustrative purposes only and that various modifications or changes in light thereof will be suggested to persons skilled in the art and are to be included within the spirit and purview of this application.

EXAMPLES

Example 1

Figure 1B:
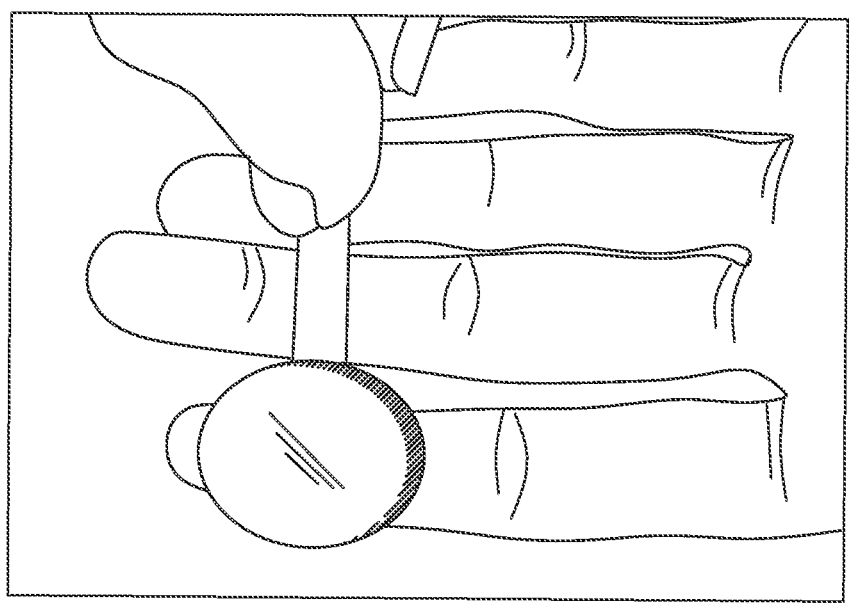
FIG. 1B shows the source and detector placed on the finger.
Figure 1C:
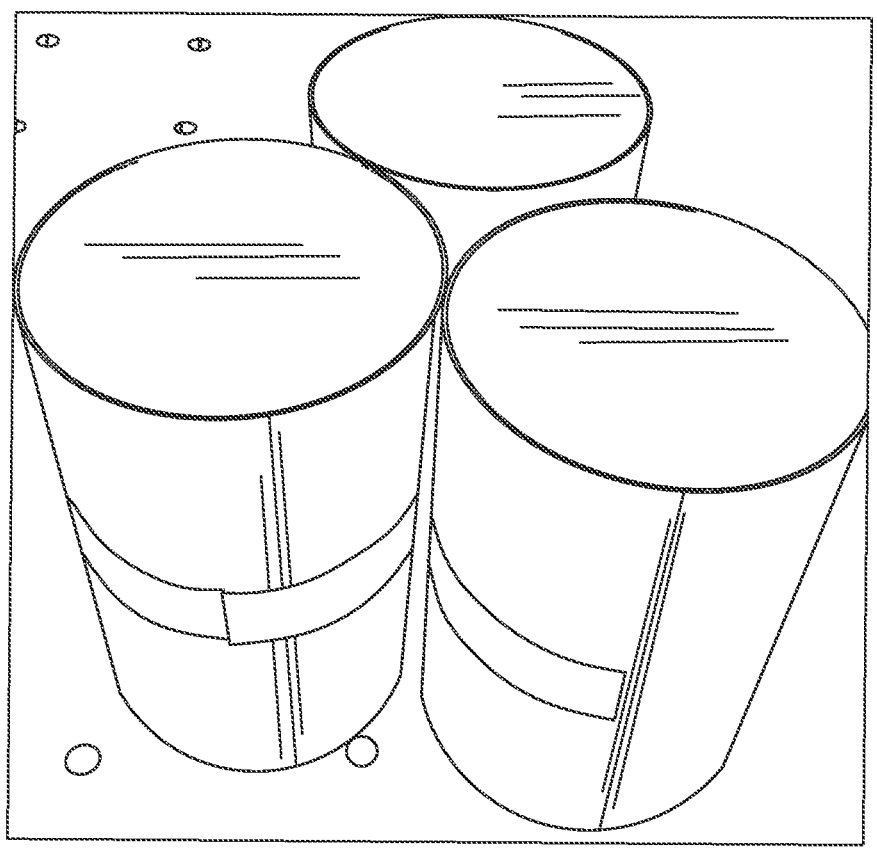
FIG. 1C shows tissue phantoms.

FIG. 1A shows an Ocean Optics Spectrometer that has been used for measurements. FIG. 1B shows the light source and the detector worn on a finger. FIG. 1C shows three tissue phantoms that were used as the tissue sample for measurement of their water content and saturation of hemoglobin.

Figure 2:
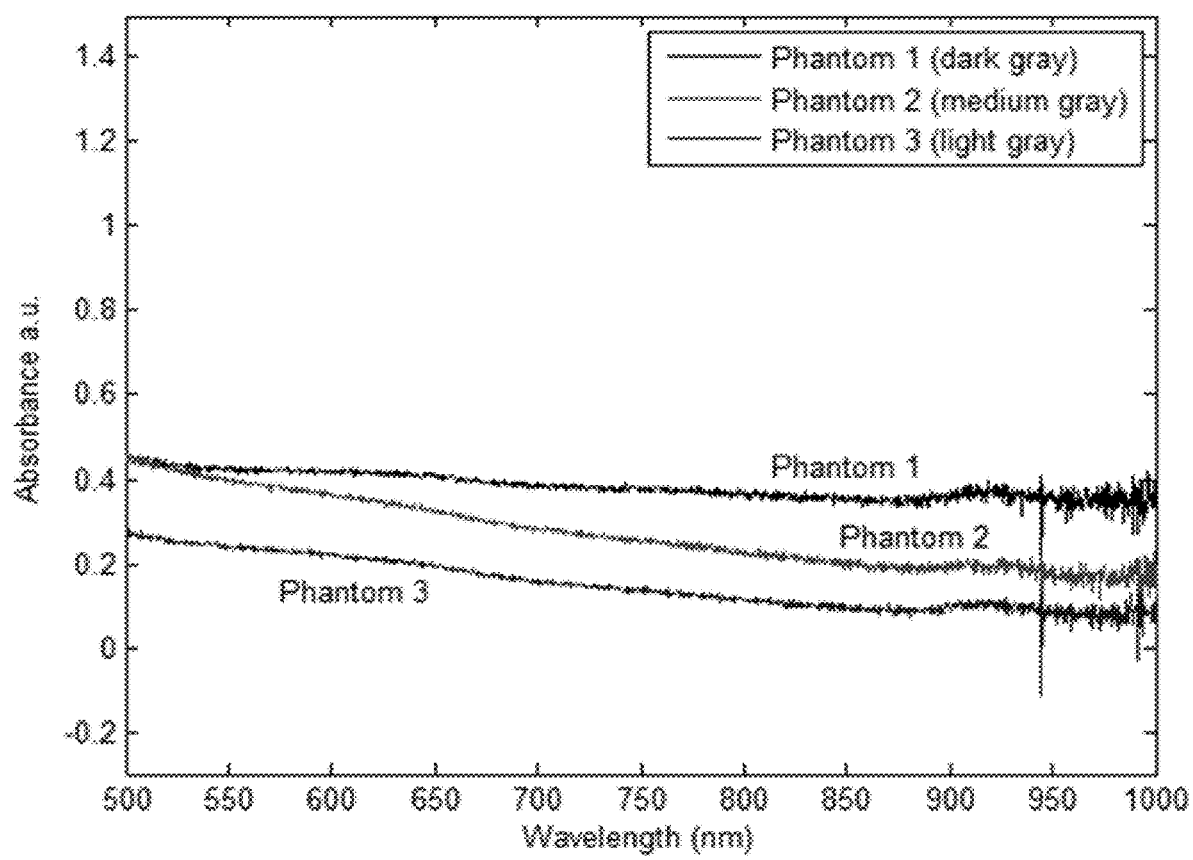
FIG. 2 shows the absorption spectrum for the three phantoms at various wavelengths.

FIG. 2 shows the absorbance spectrum for three tissue phantoms over a wavelength range of 500-1000 nm. The absorbance spectra were measured by the CDS.

FIG. 3 shows the occlusion of the blood flow (i.e., oxygen saturation of hemoglobin) measured in the finger under four conditions including normal blood flow condition and three restricted blood flow conditions. The result shows a wavelength range of 500-1000 nm. The wavelength for skin hemoglobin absorption is at its maximum between 560 nm and 580 nm.

The optical results obtained from three tissue phantoms provide the baseline for comparison with that obtained from the finger.

Example 2

Figure 4:
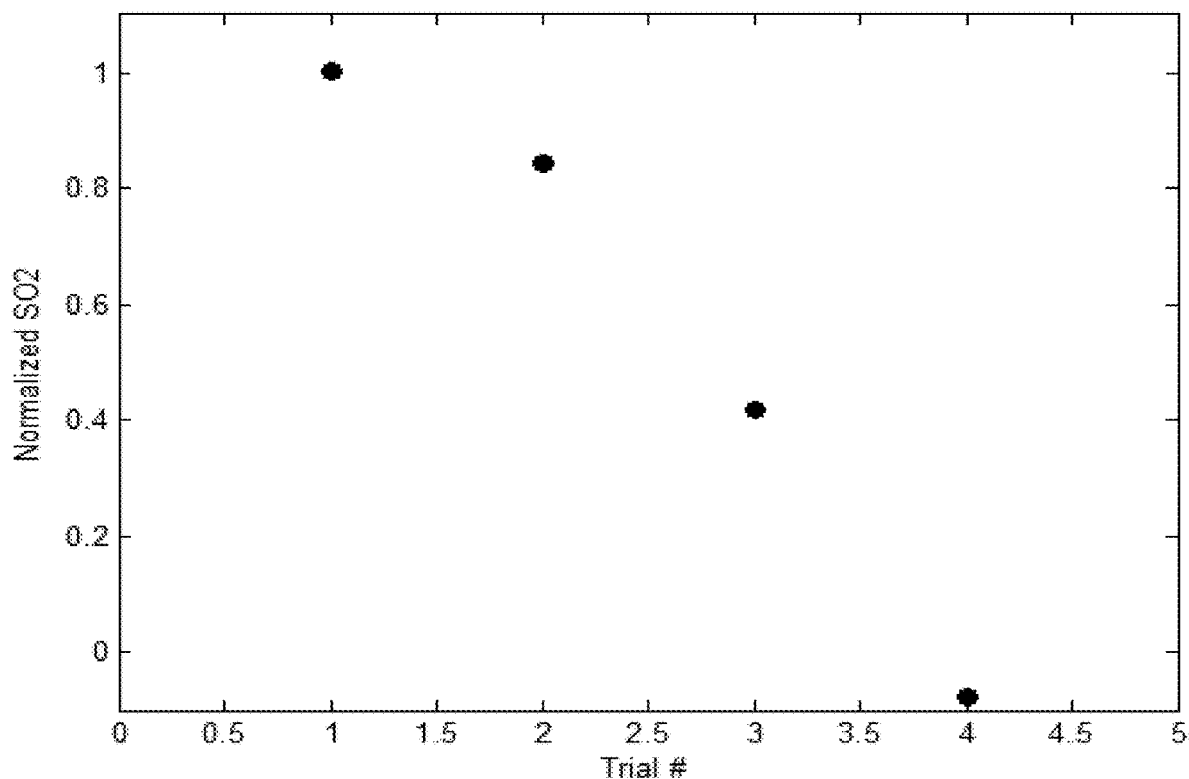
FIG. 4 shows the oxygen saturation of hemoglobin measured in the finger.

FIG. 4 shows the normalized oxygen saturation of hemoglobin in the finger over time. The first measurement was taken during full oxygenation. Then, blood flow was restricted and further measurements were taken at different time intervals until an oxygen saturation of 0 was obtained.

Example 3

Figure 5:
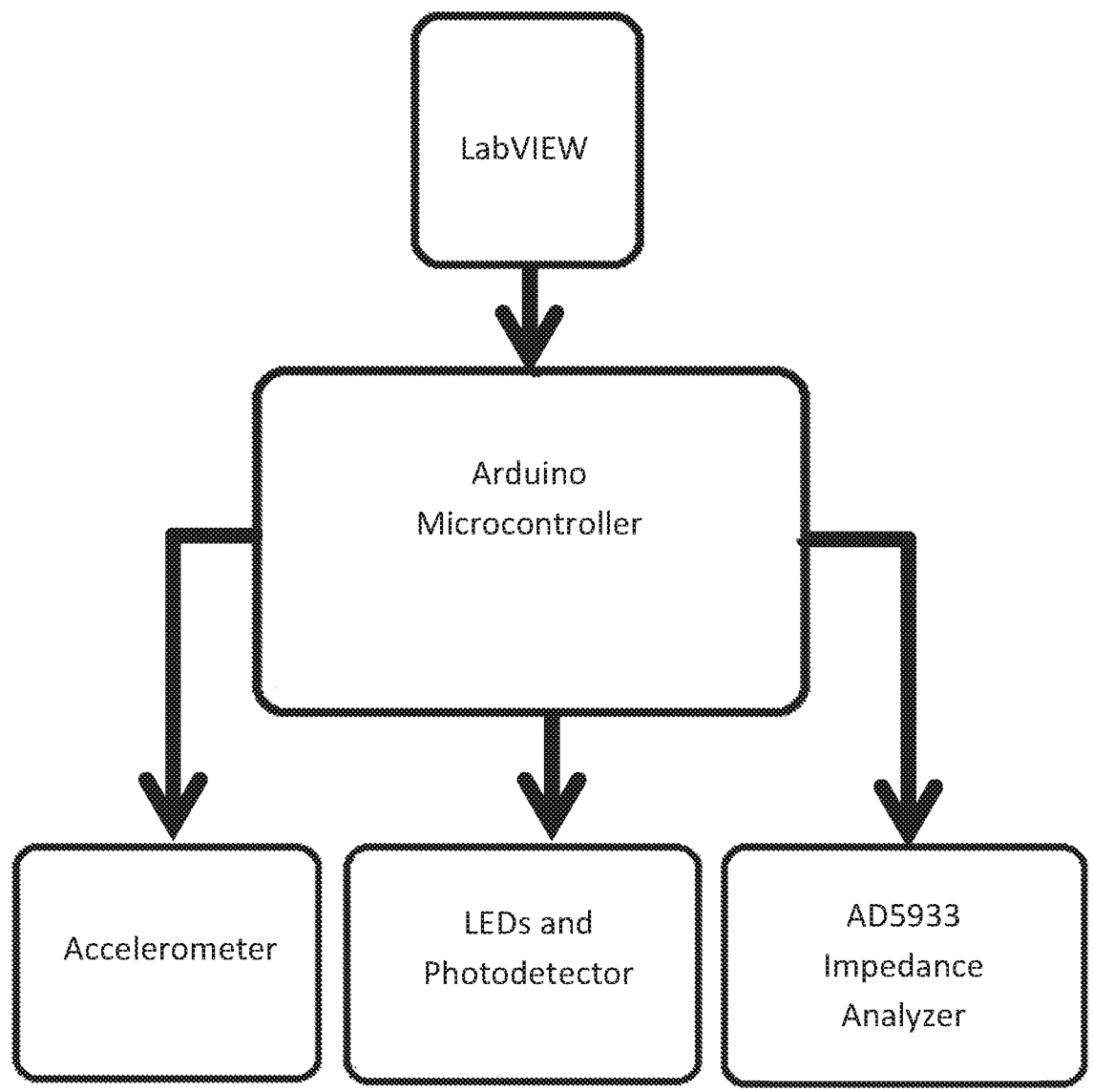
FIG. 5 shows Device 1.

FIG. 5 illustrates a flowchart of a sample CDS Device. This device is a portable device that measures skin and water content with an impedance analyzer evaluation board, blood flow occlusion with LEDs and a photodetector, and motion with an accelerometer.

Example 4

FIG. 6 illustrates a flowchart of another sample CDS Device. This device is a smaller and stand-alone portable device that measures skin and water content with an impedance analyzer chip, blood flow occlusion with LEDs and a photodetector, and motion with an accelerometer.

Example 5

The CDS device can be a wearable form that may be worn by the patient on the affected limb. Further optimization of the design can involve, for example, a baseline measurement for the electrical component using the Delfin MoistureMeter D, and programming of all the components.

REFERENCES

1. K. L. McCance and S. E. Huether, Pathophysiology: The biologic basis for disease in adults and children: Elsevier Health Sciences, 2014.
2. S. G. Rockson, "Lymphedema," American Journal of Medicine, vol. 110, pp. 288-295, March 2001.
3. E. Daniel-Spiegel, et al., "Hydrops fetalis: an unusual prenatal presentation of hereditary congenital lymphedema," Prenat Diagn, vol. 25, pp. 1015-8, November 2005.
4. C. Bellini, et al., "Lymphatic dysplasias in newborns and children: the role of lymphoscintigraphy," J Pediatr, vol. 152, pp. 587-9, 589 e1-3, April 2008.
5. A. K. Greene and C. C. Schook, "Primary lymphedema: definition of onset based on developmental age," Plast Reconstr Surg, vol. 129, pp. 221e-222e, January 2012.
6. J. M. Lewis and E. R. Wald, "Lymphedema praecox," J Pediatr, vol. 104, pp. 641-8, May 1984.
7. C. Rizzo, et al., "Lymphedema praecox," Dermatol Online J, vol. 15, p. 7, 2009.
8. G. Murdaca, et al., "Current views on diagnostic approach and treatment of lymphedema," American Journal of Medicine, vol. 125, pp. 134-40, February 2012.
9. E. S. Wheeler, et al., "Familial lymphedema praecox: Meige's disease," Plast Reconstr Surg, vol. 67, pp. 362-4, March 1981.
10. A. Zimmermann, et al., "Efficacy of manual lymphatic drainage in preventing secondary lymphedema after breast cancer surgery," Lymphology, vol. 45, pp. 103-12, September 2012.
11. C. Miaskowski, et al., "Lymphatic and angiogenic candidate genes predict the development of secondary lymphedema following breast cancer surgery," Plos One, vol. 8, p. e60164, 2013.
12. D. N. Finegold, et al., "Connexin 47 mutations increase risk for secondary lymphedema following breast cancer treatment," Clin Cancer Res, vol. 18, pp. 2382-90, Apr. 15, 2012.

13. M. Oremus, et al., "Systematic review: conservative treatments for secondary lymphedema," Bmc Cancer, vol. 12, p. 6, 2012.
14. L. M. Zeldenryk, et al., "The emerging story of disability associated with lymphatic filariasis: a critical review," PLoS Negl Trop Dis, vol. 5, p. e1366, December 2011.
15. N. H. Cox, "Oedema as a risk factor for multiple episodes of cellulitis/erysipelas of the lower leg: a series with community follow-up," British Journal of Dermatology, vol. 155, pp. 947-950, November 2006.
16. P. C. Woo, et al., "Cellulitis complicating lymphoedema," Eur J Clin Microbiol Infect Dis, vol. 19, pp. 294-7, April 2000.
17. W. M. Zhang, et al., "Multidimensional femtosecond correlation spectroscopies of electronic and vibrational excitons," Journal of Chemical Physics, vol. 110, pp. 5011-5028, Mar. 15, 1999.
18. S. Mukamel and D. Abramavicius, "Many-body approaches for simulating coherent nonlinear spectroscopies of electronic and vibrational excitons," Chem Rev, vol. 104, pp. 2073-98, April 2004.

We claim:

1. A coupled domain sensor device for quantification of skin hydration and occlusion of blood flow of a subject, the coupled domain sensor comprising:
    an electrical component, the electrical component comprising at least two electrodes and an impedance analyzer electrically connected to the two electrodes, and
    an optical component, the optical component comprising a light source and a photodetector;
    the coupled domain sensor device further comprising a microcontroller,
    the impedance analyzer performing a single frequency bioelectrical impedance analysis at a single frequency in a range of 0.5 kHz to 2000 kHz and performing a multifrequency bioelectrical impedance analysis at different frequencies in a range of 0.5 kHz to 1000 kHz, by sending an alternating current in a range of 1 μA to 2000 μA, the multifrequency bioelectrical impedance analysis comprising quantifying an amount of extracellular water at a frequency in a range of 1 kHz to 5 kHz and quantifying an amount of total body water at a frequency in a range of 100 kHz to 500 kHz,
    the electrical component being configured to measure the skin hydration and the optical component being configured to measure saturation of hemoglobin, which is indicative of the occlusion of blood flow, and
    the coupled domain sensor device being configured to diagnose fluid build-up if a measured level of skin hydration is at least 5% higher than that of a control sample and to diagnose occlusion of blood flow if a measured level of saturation of hemoglobin is at least 5% less than that of the control sample.

2. The coupled domain sensor device according to claim 1, further comprising an accelerometer.

3. The coupled domain sensor device according to claim 1, the impedance analyzer being an impedance analyzer evaluation board or an impedance analyzer chip.

4. The coupled domain sensor device according to claim 1, the light source being an LED or a laser.

5. The coupled domain sensor device according to claim 1, the photodetector being a spectrometer.

6. The coupled domain sensor device according to claim 1, which is portable.

7. The coupled domain sensor device according to claim 1, which is adapted to be a body-worn device.

8. The coupled domain sensor device according to claim 7, which is adapted to be a limb-worn device, a finger-worn device, or a toe-worn device.

9. A method for measuring skin hydration and occlusion of blood flow in a subject, the method comprising:
    a) attaching the coupled domain sensor device of claim 1 to a body part of the subject, and
    b) measuring the skin hydration and saturation of hemoglobin with said device by performing the single frequency bioelectrical impedance analysis at the single frequency in the range of 0.5 kHz to 2000 kHz in the impedance analyzer of the coupled domain sensor device and performing the multifrequency bioelectrical impedance analysis at different frequencies in the range of 0.5 kHz to 1000 kHz in the impedance analyzer of the coupled domain sensor device, by sending the alternating current in the range of 1 μA to 2000 μA, the multifrequency bioelectrical impedance analysis comprising quantifying an amount of extracellular water at a frequency in a range of 1 kHz to 5 kHz and quantifying an amount of total body water at a frequency in a range of 100 kHz to 500 kHz,
    the skin hydration being measured by the electrical component and the saturation of hemoglobin being measured by the optical component.

10. The method according to claim 9, the body part being a limb, finger, or toe.

11. The method according to claim 9, the subject being a human.

12. A method for predicting fluid build-up and occlusion of blood flow in a subject with edema, the method comprising:
    a) attaching the coupled domain sensor device of claim 1 to a body part of a subject,
    b) measuring the skin hydration and saturation of hemoglobin with said device by performing the single frequency bioelectrical impedance analysis at the single frequency in the range of 0.5 kHz to 2000 kHz in the impedance analyzer of the coupled domain sensor device and performing the multifrequency bioelectrical impedance analysis at different frequencies in the range of 0.5 kHz to 1000 kHz in the impedance analyzer of the coupled domain sensor device, by sending the alternating current in the range of 1 μA to 2000 μA, the multifrequency bioelectrical impedance analysis comprising quantifying an amount of extracellular water at a frequency in a range of 1 kHz to 5 kHz and quantifying an amount of total body water at a frequency in a range of 100 kHz to 500 kHz, to obtain a measured level of skin hydration and a measured level of saturation of hemoglobin,
    c) comparing the measured levels of skin hydration and saturation of hemoglobin to those of the control sample, and
    d) determining the likelihood of fluid build-up and occlusion of blood flow based on the comparison of step c),
    the skin hydration being measured by the electrical component and the saturation of hemoglobin being measured by the optical component, and
    the determining the likelihood of fluid build-up and occlusion of blood flow comprising diagnosing fluid build-up if the measured level of skin hydration is at least 5% higher than that of the control sample and diagnosing occlusion of blood flow if the measured level of saturation of hemoglobin is at least 5% less than that of the control sample.

13. The method according to claim 12, the body part being a limb, finger, or toe.

14. The method according to claim 12, the subject being a human.

15. A method for monitoring skin hydration and occlusion of blood flow in a subject, the method comprising:
   a) attaching the coupled domain sensor device of claim 1 to a body part of the subject, and
   b) monitoring the skin hydration and saturation of hemoglobin with said device by performing the single frequency bioelectrical impedance analysis at the single frequency in the range of 0.5 kHz to 2000 kHz in the impedance analyzer of the coupled domain sensor device and performing the multifrequency bioelectrical impedance analysis at different frequencies in the range of 0.5 kHz to 1000 kHz in the impedance analyzer of the coupled domain sensor device, by sending the alternating current in the range of 1 μA to 2000 μA, the multifrequency bioelectrical impedance analysis comprising quantifying an amount of extracellular water at a frequency in a range of 1 kHz to 5 kHz and quantifying an amount of total body water at a frequency in a range of 100 kHz to 500 kHz,
   the skin hydration being measured by the electrical component and the saturation of hemoglobin being measured by the optical component.

16. The method according to claim 15, the body part being a limb, finger, or toe.

17. The method according to claim 15, the subject being a human.

18. A method for improving treatment for edema, the method comprising:
   a) attaching the coupled domain sensor device of claim 2 to a body part of the subject;
   b) monitoring skin hydration and saturation of hemoglobin with said device by performing the single frequency bioelectrical impedance analysis at the single frequency in the range of 0.5 kHz to 2000 kHz in the impedance analyzer of the coupled domain sensor device and performing the multifrequency bioelectrical impedance analysis at different frequencies in the range of 0.5 kHz to 1000 kHz in the impedance analyzer of the coupled domain sensor device, by sending the alternating current in the range of 1 μA to 2000 μA, the multifrequency bioelectrical impedance analysis comprising quantifying an amount of extracellular water at a frequency in a range of 1 kHz to 5 kHz and quantifying an amount of total body water at a frequency in a range of 100 kHz to 500 kHz;
   c) measuring movements of the subject with the accelerometer;
   d) correlating movements of the subject with changes in the skin hydration and/or saturation of hemoglobin; and
   e) having the subject increase movements that improve skin hydration and/or saturation of hemoglobin,
   the skin hydration being measured by the electrical component and the saturation of hemoglobin being measured by the optical component.

19. The coupled domain sensor device according to claim 1, the light source and the photodetector being spaced apart from each other by a distance in a range of from 0.8 mm to 3.0 mm.

20. The coupled domain sensor device according to claim 19, the single frequency bioelectrical impedance analysis being performed at the single frequency of 50 kHz.

* * * * *